United States Patent
Avnery

(10) Patent No.: US 7,547,892 B2
(45) Date of Patent: *Jun. 16, 2009

(54) AIR STERILIZING SYSTEM

(75) Inventor: Tzvi Avnery, Winchester, MA (US)

(73) Assignee: Advanced Electron Beams, Inc., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/703,620

(22) Filed: Feb. 7, 2007

(65) Prior Publication Data

US 2007/0145291 A1    Jun. 28, 2007

Related U.S. Application Data

(60) Continuation of application No. 11/122,334, filed on May 4, 2005, now Pat. No. 7,189,978, which is a continuation-in-part of application No. 10/666,380, filed on Sep. 19, 2003, now Pat. No. 7,323,137, which is a division of application No. 09/883,861, filed on Jun. 18, 2001, now Pat. No. 6,623,706.

(60) Provisional application No. 60/213,358, filed on Jun. 20, 2000.

(51) Int. Cl.
*G01N 21/00* (2006.01)
*C01B 3/00* (2006.01)

(52) U.S. Cl. ............... 250/455.11; 250/454.11; 204/158.2; 204/157.3

(58) Field of Classification Search ............ 250/492.3, 250/455.11; 422/186; 204/157.3; 356/500
See application file for complete search history.

(56) References Cited

U.S. PATENT DOCUMENTS 3,105,733 A    10/1963  Potapenko
3,779,706 A    12/1973  Nablo
3,869,362 A     3/1975  Machi et al.
4,167,466 A     9/1979  Orr, Jr. et al.
4,244,712 A     1/1981  Tongret
4,324,759 A     4/1982  Aoki et al.
4,396,580 A     8/1983  Patrick et al.
4,507,265 A     3/1985  Higo et al.
4,595,569 A     6/1986  Reuter et al.
4,752,450 A     6/1988  Dietrich et al.

(Continued)

FOREIGN PATENT DOCUMENTS

EP    0 579 105 A1    1/1994

(Continued)

OTHER PUBLICATIONS

Tian, C., and Vidal, C.R., "Single to Quadruple Ionization of $CO_2$ Due to Electron Impact," *Phys. Rev. A*, 58(5): 3783-3795 (1998).

(Continued)

*Primary Examiner*—Nikita Wells
*Assistant Examiner*—Johnnie L Smith
(74) *Attorney, Agent, or Firm*—Hamilton, Brook, Smith & Reynolds, P.C.

(57) ABSTRACT

A system for sterilizing air includes an air duct for flowing the air therethrough. A first electron beam generator is positioned relative to the duct for irradiating the air flowing therethrough with a first electron beam. The first electron beam for disabling biological substances within the air.

18 Claims, 12 Drawing Sheets

U.S. PATENT DOCUMENTS

| | | | |
|---|---|---|---|
| 4,882,020 A | 11/1989 | Maezawa et al. | |
| 4,915,916 A * | 4/1990 | Ito et al. | 422/186 |
| 4,961,830 A | 10/1990 | Aoki et al. | |
| 4,969,984 A | 11/1990 | Kawamura et al. | |
| 5,015,442 A | 5/1991 | Hirai | |
| 5,015,443 A * | 5/1991 | Ito et al. | 422/186 |
| 5,041,271 A | 8/1991 | Aoki et al. | |
| 5,112,370 A | 5/1992 | Gazzano | |
| 5,244,552 A | 9/1993 | Namba et al. | |
| 5,319,211 A | 6/1994 | Matthews et al. | |
| 5,357,291 A | 10/1994 | Schonberg et al. | |
| 5,368,816 A | 11/1994 | Detzer | |
| 5,378,898 A * | 1/1995 | Schonberg et al. | 250/492.3 |
| 5,382,410 A | 1/1995 | Peltier | |
| 5,445,798 A | 8/1995 | Ikeda et al. | |
| 5,457,269 A | 10/1995 | Schonberg | |
| 5,468,356 A | 11/1995 | Uhm | |
| 5,468,454 A | 11/1995 | Kim | |
| 5,484,570 A | 1/1996 | Ikeda et al. | |
| 5,523,577 A | 6/1996 | Schonberg et al. | |
| 5,527,459 A | 6/1996 | Ikeda et al. | |
| 5,539,212 A | 7/1996 | Matthews et al. | |
| 5,573,730 A | 11/1996 | Gillum | |
| 5,582,807 A | 12/1996 | Liao et al. | |
| 5,656,242 A | 8/1997 | Morrow et al. | |
| 5,693,195 A | 12/1997 | Saito et al. | |
| 5,695,616 A | 12/1997 | Helfritch et al. | |
| 5,700,311 A | 12/1997 | Spencer | |
| 5,702,572 A | 12/1997 | Fujimura et al. | |
| 5,744,811 A | 4/1998 | Schonberg et al. | |
| 5,756,054 A | 5/1998 | Wong et al. | |
| 5,759,487 A | 6/1998 | Jung | |
| 5,770,785 A | 6/1998 | Tamura et al. | |
| 5,801,387 A | 9/1998 | Nablo et al. | |
| 5,811,014 A | 9/1998 | Green et al. | |
| 5,834,722 A | 11/1998 | Tokunaga et al. | |
| 5,837,207 A | 11/1998 | Summers | |
| 5,853,680 A | 12/1998 | Iijima et al. | |
| 5,861,127 A | 1/1999 | Yeh | |
| 5,894,130 A | 4/1999 | Bach | |
| 5,925,320 A | 7/1999 | Jones | |
| 5,933,702 A | 8/1999 | Goswami | |
| 5,939,026 A | 8/1999 | Seki et al. | |
| 5,993,612 A | 11/1999 | Rostaing et al. | |
| 6,077,488 A | 6/2000 | Jain et al. | |
| 6,080,281 A | 6/2000 | Attia | |
| 6,179,968 B1 | 1/2001 | Izutsu et al. | |
| 6,210,642 B1 | 4/2001 | Lee et al. | |
| 6,328,937 B1 | 12/2001 | Glazman | |
| 6,623,706 B2 | 9/2003 | Avnery | |
| 6,893,610 B1 | 5/2005 | Barnes | |
| 7,189,978 B2 * | 3/2007 | Avnery | 250/455.11 |
| 7,323,137 B2 * | 1/2008 | Avnery | 422/24 |
| 2002/0005345 A1 | 1/2002 | Avnery | |
| 2002/0011405 A1 | 1/2002 | Avnery | |
| 2003/0086831 A1 | 5/2003 | Horton, III | |
| 2004/0060811 A1 | 4/2004 | Avnery | |
| 2004/0147214 A1 * | 7/2004 | Oono | 454/187 |

FOREIGN PATENT DOCUMENTS

| | | |
|---|---|---|
| EP | 1 376 021 A1 | 1/2004 |
| GB | 2 173 779 A | 10/1986 |
| GB | 2 341 094 A | 3/2000 |
| JP | 63302924 | 12/1988 |
| WO | WO 97/01386 | 1/1997 |
| WO | WO 00/64499 | 11/2000 |

OTHER PUBLICATIONS

Darici, Y., et al. "Electron Beam Dissociation of CO and $CO_2$ on ZnS Thin Films," *J. Vac. Sci. Technol. A*, 17(3), 692-697 (1999).

* cited by examiner

AIR STERILIZING SYSTEM

RELATED APPLICATIONS

This application is a continuation of U.S. application Ser. No. 11/122,334, filed May 4, 2005, now U.S. Pat. No. 7,189,978 which is a continuation-in-part of U.S. application Ser. No. 10/666,380, filed Sep. 19, 2003, now U.S. Pat. No. 7,323,137 which is a divisional of U.S. application Ser. No. 09/883,861, filed Jun. 18, 2001, now U.S. Pat. No. 6,623,706, issued Sep. 23, 2003, which claims the benefit of U.S. Provisional Application No. 60/213,358, filed on Jun. 20, 2000. The entire teachings of the above applications are incorporated herein by reference.

BACKGROUND

Air circulation systems, for example, air conditioning and heating systems in buildings and aircraft, have been known to circulate airborne viruses and bacteria, spreading sickness to the occupants. This is becoming a concern to both the manufacturers of such systems as well as the occupants. Some air circulation systems in buildings are beginning to address this problem by including an air sterilization system therein for sterilizing the air. Typically, in such systems, the air is sterilized by irradiating the circulating air with ultraviolet lights. A drawback of this method is that the sterilization process is dependent upon the time of exposure to the ultraviolet light, and therefore, the effectiveness decreases with increasing air velocity. In addition, dust collecting on the ultraviolet lights reduces the intensity of the ultraviolet light that irradiates the air, which further reduces the effectiveness of the sterilization process.

SUMMARY

The present invention provides a system for sterilizing air that is more effective than prior methods, and includes a duct for flowing the air therethrough. A first electron beam generator is positioned relative to the duct for irradiating the air flowing therethrough with a first electron beam. The first electron beam disables or kills microorganisms within the air such as viruses, bacteria, fungi, etc., to sterilize the air.

In preferred embodiments, an air circulator for causing air to flow through the duct can be included. In addition, the system can be in or form an air circulation system. A converter is positioned within the duct downstream from the first electron beam generator for converting ozone within the air into oxygen. In one embodiment, a reflector is in the duct opposite to the first electron beam generator for reflecting the first electron beam. In another embodiment, a second electron beam generator is positioned relative to the duct opposite to the first electron beam generator for irradiating the air flowing through the duct with a second electron beam. In yet another embodiment, the duct has two right angle turns on opposite sides of the first electron beam generator for providing shielding from radiation. This duct can be collimated. In still another embodiment, at least a portion of the duct can form a sterilization chamber. The air can be directed into the sterilization chamber generally against the direction of the electron beam and then be redirected generally along the direction of the electron beam for irradiating the air.

The present invention is also directed to a method of sterilizing air which includes flowing the air through a duct and irradiating the air flowing through the duct with a first electron beam from a first electron beam generator. The first electron beam disables microorganisms within the air to sterilize the air. The sterilization can occur in an air circulation system.

Additionally, the present invention is directed to a method for sterilizing air including flowing the air through a duct and irradiating the flowing air with opposed first and second electron beams from first and second electron beam generators for disabling microorganisms in the air. The first and second electron beam generators are positioned relative to the duct opposite from each other.

The present invention is further directed to a method of sterilizing air including directing an electron beam into a sterilization chamber. The air is directed into the sterilization chamber generally against the direction of the electron beam and is redirected generally along the direction of the electron beam for irradiating the air and disabling microorganisms in the air.

The use of an electron beam to sterilize air in the present invention provides more effective sterilization of flowing air than prior methods such as irradiation with ultraviolet light because electron beams can disable or kill microorganisms more rapidly. In addition, electron beams are affected by dust to a lesser degree than ultraviolet light. Consequently, the present invention can effectively sterilize air flowing at high flow rates.

Embodiments in the present invention can employ an electron beam or beams to destroy or disable, in more general terms, biological substances within air. Biological substances include microorganisms and further include biological fragments, materials or products, for example, biological poisons, proteins, pyrogens, etc. Embodiments of the present invention, when disabling biological substances such as pyrogens, can vaporize or oxidize at least some of the pyrogens.

BRIEF DESCRIPTION OF THE DRAWINGS

The foregoing and other objects, features and advantages of the invention will be apparent from the following more particular description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
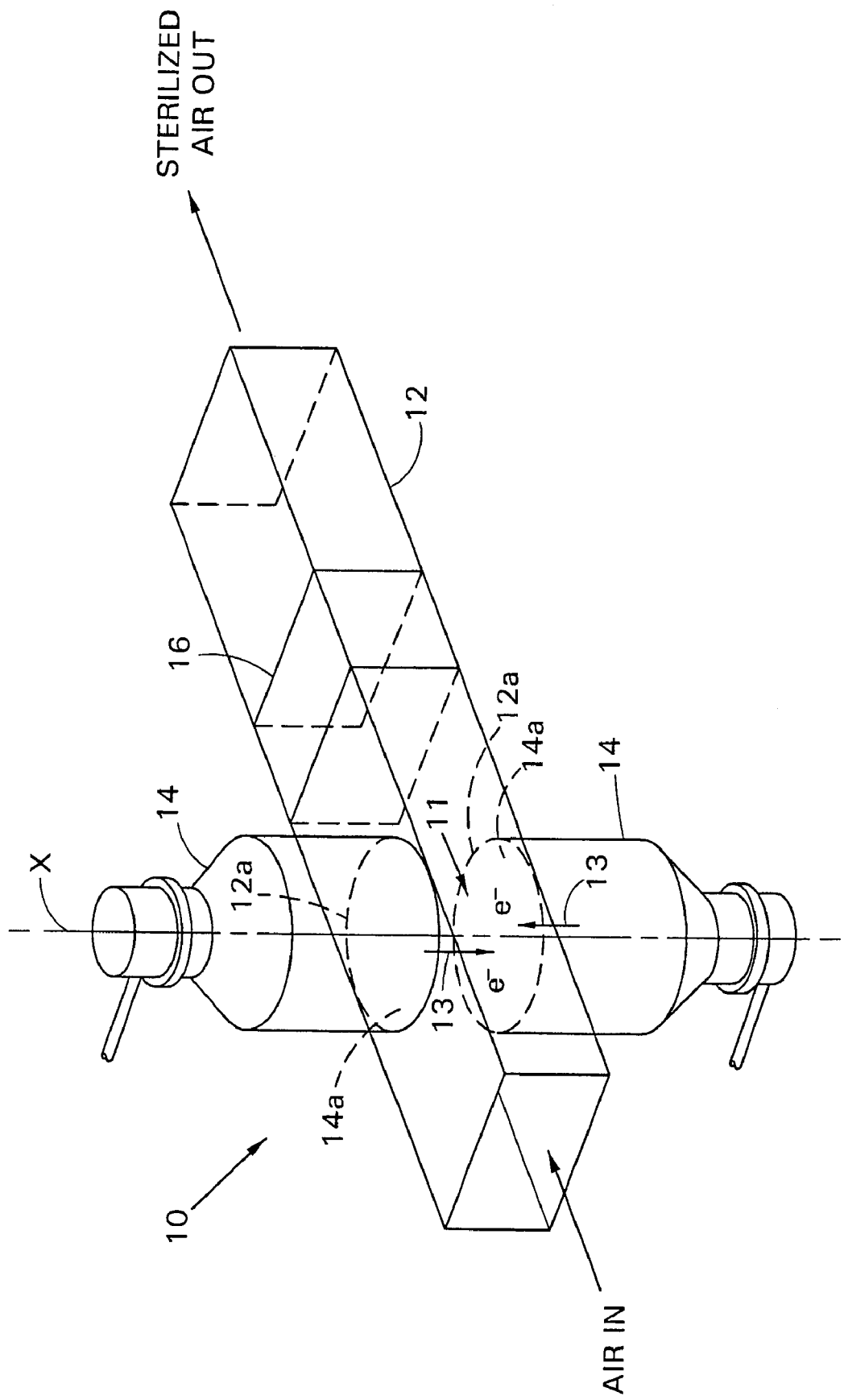
FIG. 1 is a perspective schematic drawing of an embodiment of the present invention air sterilizing system.

Referring to FIG. 1, air sterilizing system 10 is employed for sterilizing breathable air and is often incorporated into or included in an air circulation system such as an air conditioning and/or heating system for killing microorganisms within the circulated air, for example, viruses, bacteria and fungi (including yeasts and molds), as well as pollen, etc. Air sterilizing system 10 can also be employed to circulate air just for sterilization purposes. Air sterilizing system 10 includes an air duct 12 which air circulates through in the direction of the arrows. Two electron beam generators 14 are positioned on opposite sides of the air duct 12, for directing electrons e- from opposed electron beams 13 into the flowing air in an irradiation zone 11 between the electron beam generators 14. The electron beam generators 14 are sized to provide complete electron beam coverage over the cross-section (width and height) of air duct 12 so that virtually all the air flowing through the air duct 12 passes through the electron beams 13. The electron beams 13 disable or kill airborne microorganisms flowing in the air by damaging the DNA and/or structural matter, thereby sterilizing the air. Any X-rays formed by electrons e- striking the walls of air duct 12 may also help disable some of the microorganisms. Typically, a converter 16 is located with air duct 12 downstream from the electron beam generators 14 for converting ozone ($O_3$) produced in the sterilization process back into oxygen ($O_2$). Consequently, when the treated air is introduced into an area occupied by people, sterile breathable air is provided.

A more detailed description of the air sterilizing system 10 now follows. The electron beams 13 are emitted into air duct 12 from the electron beam generators 14 through exit beam windows 14$a$ located at the distal ends of the electron beam generators 14. The width of air duct 12 is commonly about the same as the width of the exit beam windows 14$a$ of electron beam generators 14. The air duct 12 has two opposed holes 12$a$ which are configured with the proper size and shape to allow the electron beams 13 to enter the air duct 12. Typically, the electron beam generators 14 are mounted to air duct 12 along a common axis X and in a sealed manner which prevents radiation from escaping to the exterior of air duct 12. The electron beam generators 14 can be similar to those disclosed in U.S. Pat. No. 6,407,492, issued Jun. 18, 2002, entitled "Electron Beam Accelerator", or U.S. Pat. No. 6,545, 398, issued Apr. 8, 2003, entitled "Electron Accelerator Having a Wide Electron Beam", the contents of which are incorporated herein by reference in their entirety. Alternatively, other suitable electron beam generators may be employed. In some air circulation systems, the air duct 12 is about 8-12 inches wide by about 5-6 inches high in order to obtain a sufficient air flow rate. In one embodiment, air duct 12 is about 10 inches wide by about 5 inches wide and the electron beam generators 14 have an exit beam window 14$a$ with dimensions of about 10 inches by 3 inches. The electron beam generators 14 sized for such a duct typically operate at about 125 kV. In another embodiment, where air duct 12 is about 2 inches wide, electron beam generators 14 can be used that have a circular exit window 14$a$ that is about 2 inches in diameter and operate at about 80 kV to 100 kV.

Figure 2:
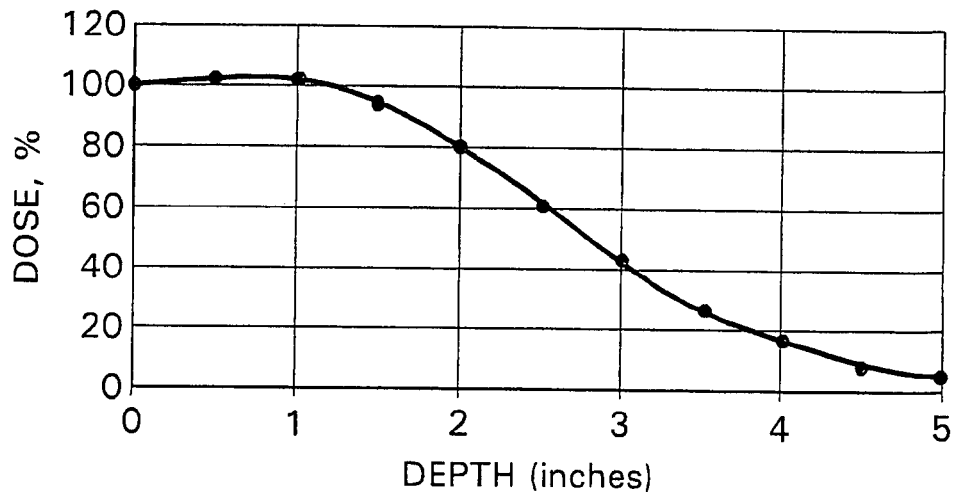
FIG. 2 is a graph depicting the energy distribution for a single electron beam directed into air.
Figure 3:
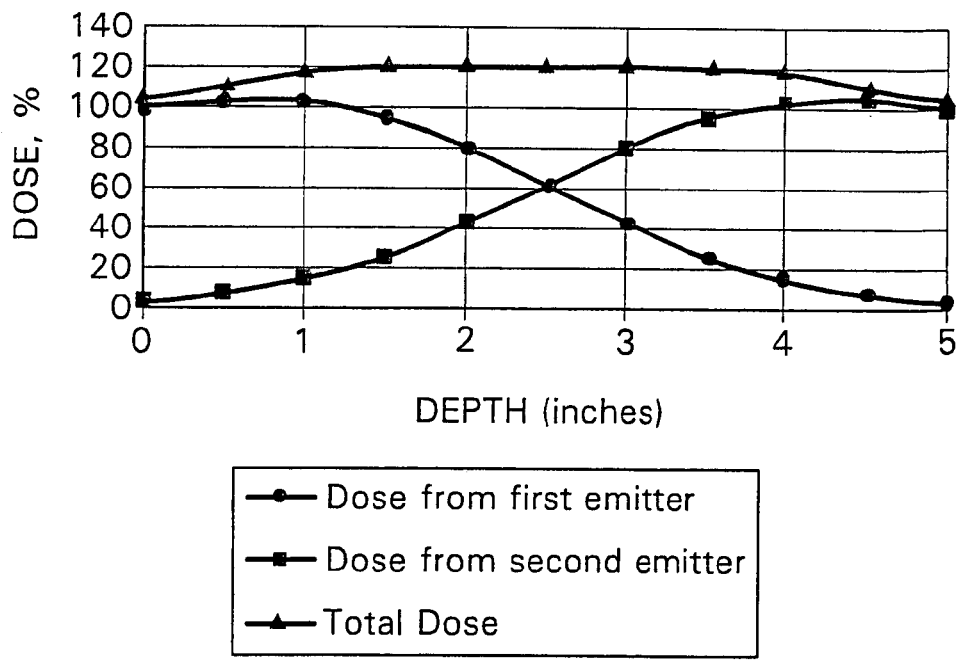
FIG. 3 is a graph depicting the energy distribution for two opposing electron beams directed into air as well as the combined energy distribution of the two beams.

For a 5-inch high air duct 12, two electron beam generators 14 operating at about 125 kV are often employed because, as can be seen in FIG. 2, the energy distribution or dose of a single electron beam 13 decreases dramatically as the electron beam 13 travels through air for an electron beam generator 14 operating at about 125 kV. For example, the electron beam 13 dose from a single electron beam generator 14 operating at about 125 kV is relatively constant for about the first 1½ inches of travel through air, but then drops rapidly at distances that are over 1½ inches. Consequently, when operating at about 125 kV, in order to obtain consistent sterilization of the air flowing through an air duct 12 that is about 10 inches by 5 inches, two opposed electron beam generators 14 are desirable. FIG. 3 shows that two electron beam generators 14 operating at about 125 kV which are positioned opposite to each other about five inches apart combine to produce a relatively constant energy distribution in the air within irradiation zone 11 of air duct 12. Although the two electron beam generators 14 are depicted as being aligned along a common axis X, alternatively, one electron beam generator 14 can be positioned or staggered downstream of the other. In a system where air duct 12 only needs to be about 1-2 inches high, the second electron beam generator 14 may be omitted. The second electron beam generator 14 may also be omitted in a higher air duct 12 (for example, 5 inches high) where consistent or total sterilization is not required.

If air duct 12 needs to be higher than 5 inches, higher power electron beam generators 14 than those specified above can be employed. In addition, lower power electron beam generators can be employed for smaller air ducts 12. The width of the electron beam generators 14 can be varied to accommodate air ducts 12 of different widths. For air ducts 12 that have dimensions that are wider than the electron beam generators 14, more than one electron beam generator 14 can be mounted side by side to irradiate the full width. The configuration of such side by side electron beam generators 14 can be aligned with each other or staggered. In addition, when extremely high air speeds are flowing through air duct 12, multiple successive electron beam generators 14 can be mounted to air duct 12 in the direction of the air flow. As a result, air flowing through air duct 12 would be irradiated by successive electron beams 13 thereby lengthening the time of irradiation to obtain the desired level of irradiation.

Converter 16 is commonly a reactive catalytic filter having a pellet bed for converting ozone flowing therethrough into oxygen. For operation at room temperature, the pellet bed typically includes spherical manganese dioxide pellets. For higher temperatures, the pellets are typically formed of platinum. The converter 16 is often positioned adjacent to the electron beam generators 14 as shown but, alternatively, can be positioned near the exit of air duct 12. When converter 16 is near the exit of a lengthy air duct 12, ozone within the flowing air formed by the electron e- irradiation can react with or neutralize any other microorganisms or contaminants that are on the walls of the air duct 12 downstream from the electron beam generators 14. In some cases, it may be desirable to omit converter 16 altogether.

Typical uses for air sterilizing system 10 are in the air circulation systems of aircraft as well as hospitals, for example, the main air circulation system, or the circulation systems for surgery or recovery rooms. Other uses include systems for hotels, schools, theaters, underground mines, malls, submarines, ships, motorized vehicles, etc.

Figure 4:
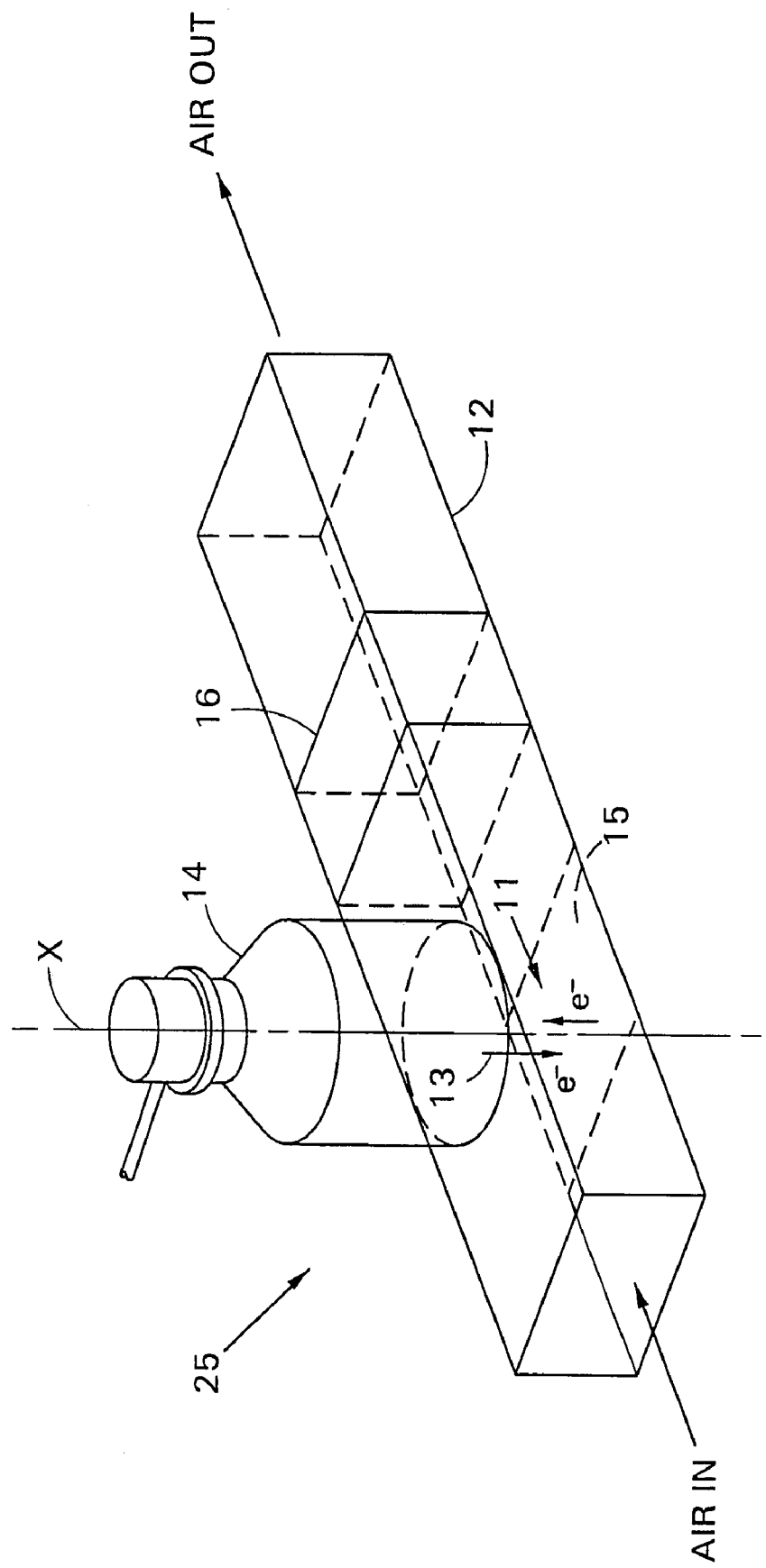
FIG. 4 is a perspective schematic view of another embodiment of the present invention air sterilizing system.
Figure 5:
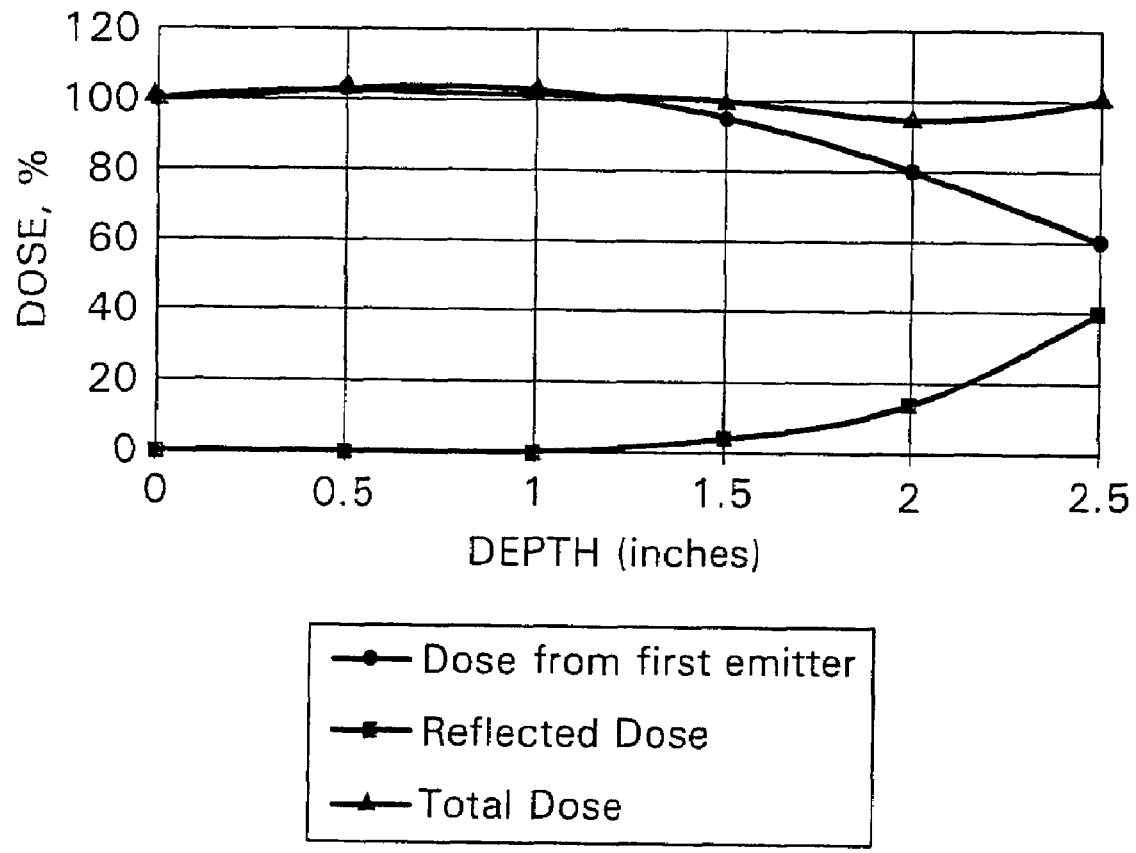
FIG. 5 is a graph depicting the energy distribution for a single electron beam directed into air, the distribution of energy that is reflected by a reflector positioned in the path of the electron beam, and the combined energy distribution of the electron beam and the reflected energy.

Referring to FIG. 4, air sterilizing system 25 is another embodiment of the present invention which differs from air sterilizing system 10 in that a single electron beam generator 14 is employed for generating a single electron beam 13 and a reflector 15 is positioned within air duct 12 on the wall opposite to the electron beam generator 14. The electron beam generator 14 and the reflector 15 are positioned along axis X with the irradiation zone 11 occupying the space or area therebetween. Some of the electrons e- from the electron beam 13 strike the reflector 15 and are reflected back into the air flowing through air duct 12 within irradiation zone 11. Typically, reflector 15 is formed from a high density material having a high Z number such as lead, or tungsten, etc. Reflector 15 can be mounted within air duct 12 or, alternatively, the air duct 12 itself can be formed of the high density material at least in the region surrounding irradiation zone 11. Referring to FIG. 5, it can be seen that the electron beam 13 and the energy reflected by the reflector 15 combine to produce a relatively constant energy distribution in the air within irradiation zone 11. For an electron beam generator 14 of about 125 kV, the graph of FIG. 5 depicts a relatively constant energy distribution for an air duct 12 having a depth or height of about 2.5 inches from the electron beam generator 14. This dimension can be increased when using an electron beam generator 14 of greater power.

Figure 6:
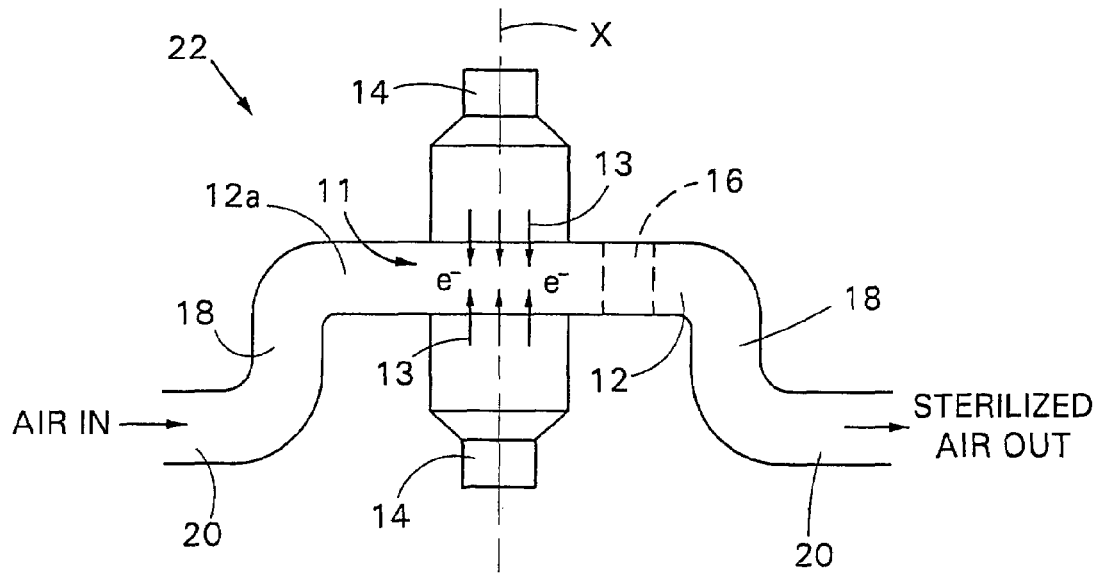
FIG. 6 is a side schematic view of still another embodiment of the present invention air sterilizing system.

Referring to FIG. 6, in still another embodiment of the present invention, air sterilizing system 22 is similar to air sterilizing system 10, differing in that air duct 12 includes two vertical legs 18 and horizontal legs 20 extending from a central duct portion 12a on opposite sides of the electron beam generators 14 for providing shielding from X-rays generated by the system. The zig zag path configuration of the legs 18 and 20 does not provide a straight path for X-rays to escape from either the entrance or exit of air duct 12. Horizontal legs 20 are typically parallel to central duct portion 12a while vertical legs 18 are at a right angle. Air duct 12, including legs 18/20, may be formed of lead or steel.

Figure 7:
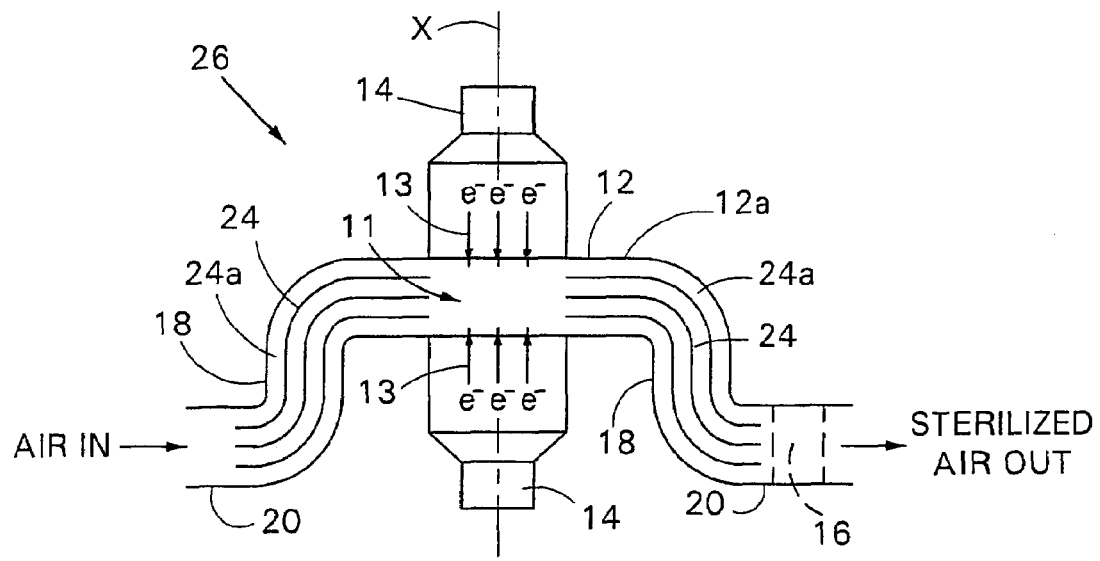
FIG. 7 is a side schematic view of yet another embodiment of the present invention air sterilizing system.

Referring to FIG. 7, in yet another embodiment of the present invention, air sterilizing system 26 differs from air sterilizing system 22 in that system 26 includes a collimation system 24 consisting of a series of small ducts 24a of laminated lead or steel extending through legs 18/20 into central duct portion 12a in a zig zag configuration. This provides better shielding of X-rays and allows the legs 18/20 and central duct portion 12a to be made much smaller than that required for air sterilizing system 22. For example, the legs 18/20 of air sterilizing system 26 may be less than one half the size of those in system 22. The converter 16 for converting ozone into oxygen is shown to be downstream from the collimation ducts 24a but, alternatively, can be upstream. Both air sterilizing systems 22 and 26 (FIGS. 6 and 7) may also include any of the features or variations previously discussed above in regard to air sterilizing systems 10 and 25. In addition, legs 18/20 can be formed at angles that are not right angles and still be in a zig zag configuration.

Figure 8:
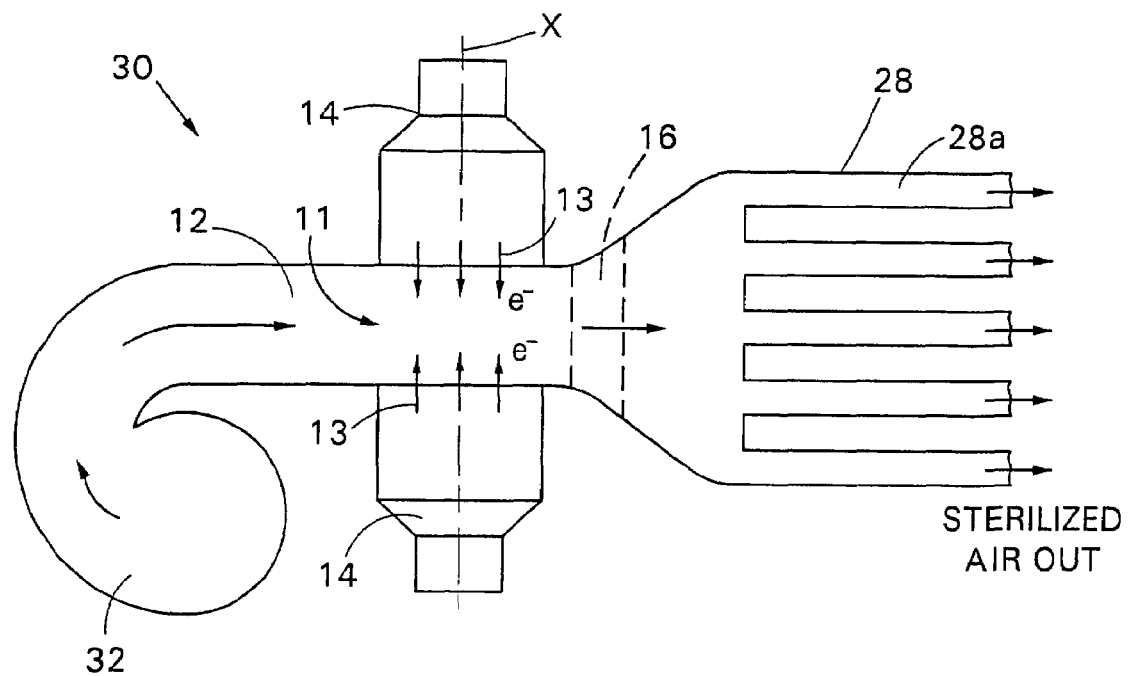
FIG. 8 is a side schematic view of still another embodiment of the present invention air sterilizing system.

Referring to FIG. 8, in still another embodiment of the present invention, air sterilizing system 30 includes an air circulator 32 such as a blower or fan for generating the air flow through air duct 12 past electron beam generators 14. A distribution junction 28 allows the sterilized air to be distributed into a series of smaller ducts 28a for distribution. A single converter 16 is shown before junction 28 for converting ozone into oxygen but, alternatively, a series of converters 16 can be positioned within each duct 28a.

Figure 9:
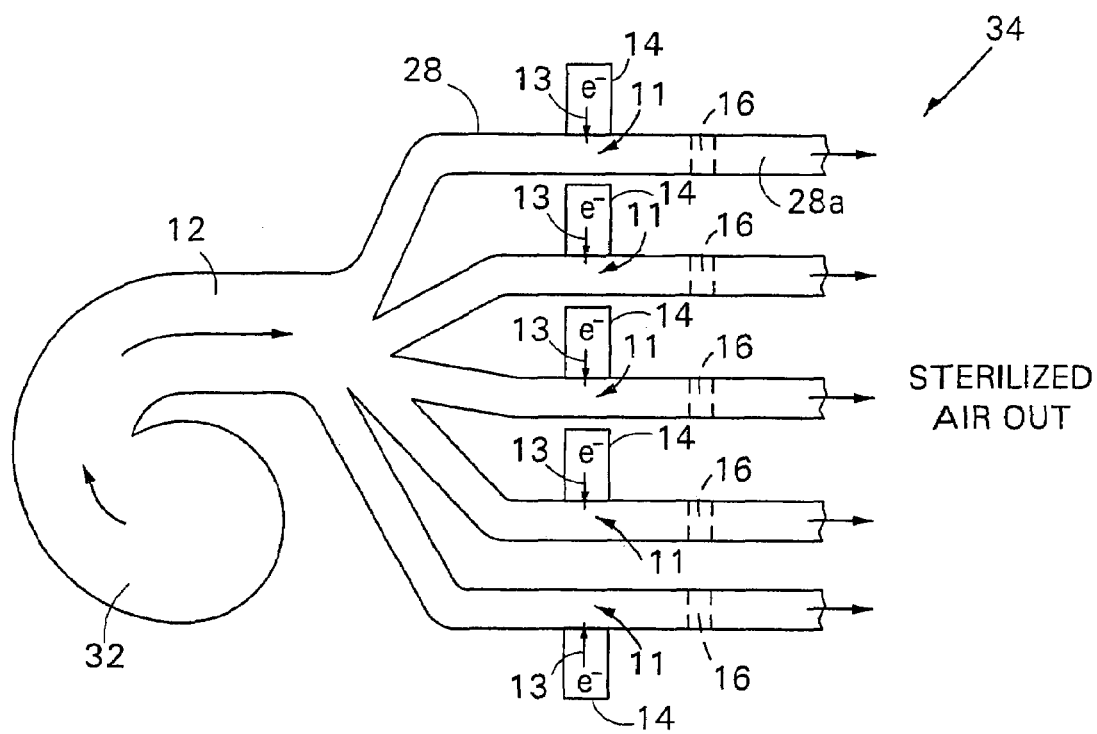
FIG. 9 is a side schematic view of another embodiment of the present invention air sterilizing system.

Referring to FIG. 9, in another embodiment of the present invention, air sterilizing system 34 differs from air sterilizing system 30 in that instead of employing two large electron beam generators 14 within air duct 12, system 34 includes a series of small electron beam generators 14 positioned along each individual duct 28a. Each duct 28a may be employed for providing air to an individual user or to separate zones. Typically, the ducts 28a are narrow enough so that only one electron beam generator 14 is required for each duct 28a but two may be used if the air ducts 28a are made larger. In addition, reflectors 15 may be employed. Both air sterilizing systems 30 and 34 can include any of the features or variations previously discussed above in regard to air sterilizing systems 10, 22, 25 and 26.

Figure 10:
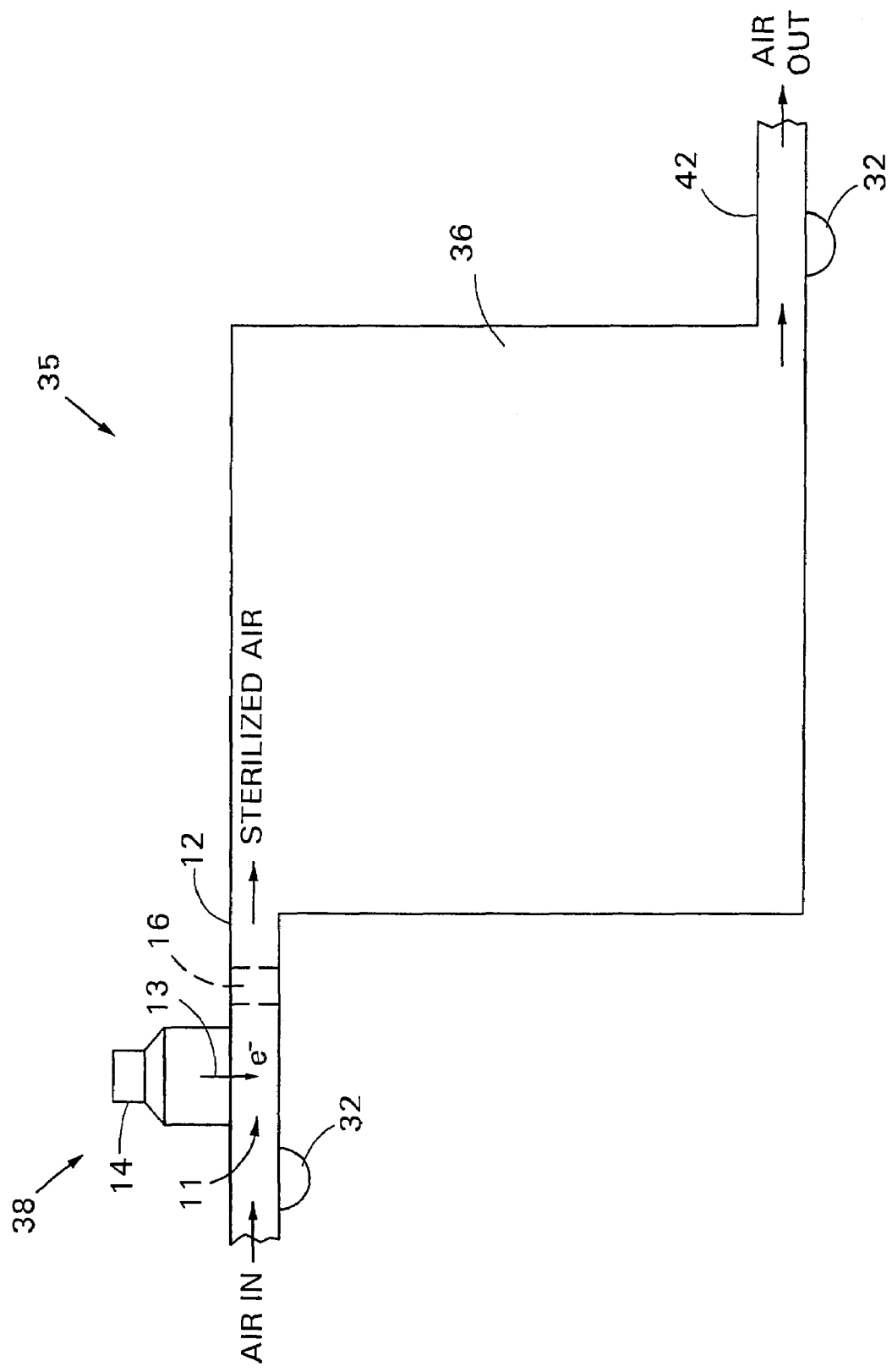
FIG. 10 is a schematic drawing of air entering an enclosed volume that is sterilized by an embodiment of the present invention air sterilizing system.

Referring to FIG. 10, in yet another embodiment, an enclosed volume 36 such as a room, hall, cabin, or building, has an air sterilizing system 35 with an air sterilizing intake system 38 for providing fresh sterilized air into the volume 36. The intake system 38 is schematically shown with only one electron beam generator 14 for simplicity and is typically similar to either air sterilizing system 10 (FIG. 1), 25 (FIG. 4), 22 (FIG. 6) or 26 (FIG. 7). An air circulator 32 forces the air into the volume 36. Air is circulated out of the volume 36 by another air circulator 32 through exhaust duct 42. If the sterilized air introduced into the volume 36 is to be directed through a series of vents spaced apart from each other, then the intake system 38 can be similar to either air sterilizing system 30 (FIG. 8) or air sterilizing system 34 (FIG. 9). In addition, if volume 36 is relatively air tight, one of the air circulators 32 can be omitted. Although the intake system 38 is shown to be at the top of volume 36 and the exhaust duct 42 at the bottom, the position and level of either can be varied to suit the situation at hand.

Figure 11:
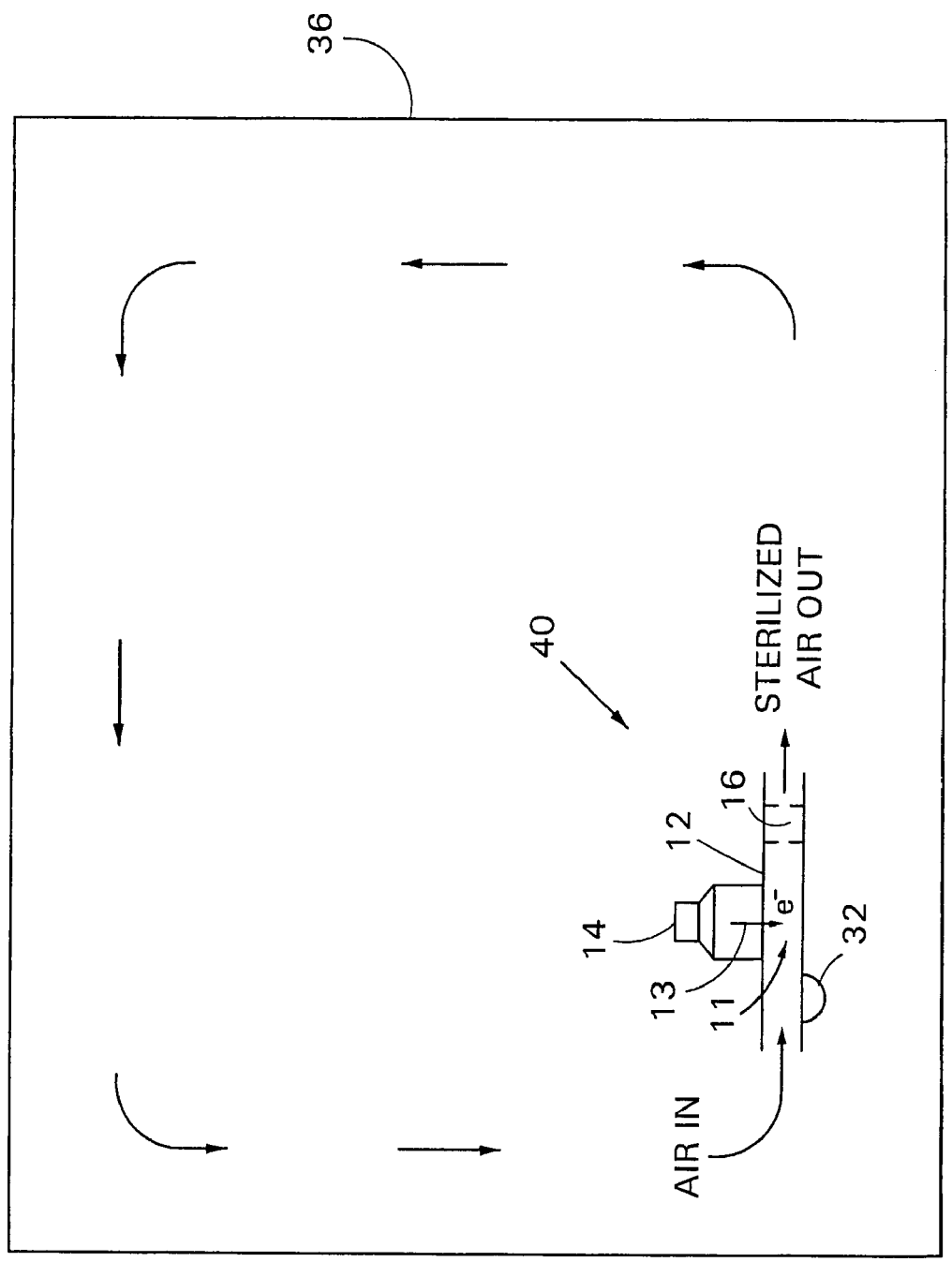
FIG. 11 is a schematic drawing of air within an enclosed volume being sterilized by an embodiment of the present invention air sterilizing system in a recirculatory manner.

Referring to FIG. 11, in another embodiment, an air sterilizing system 40 is employed within the volume 36 for circulating and sterilizing air contained within the volume 36. Air sterilizing system 40 can be similar to air sterilizing systems 10, 25, 22 or 26. In addition, when multiple delivery vents are desired, air sterilizing system 40 can be similar to either air sterilizing system 30 or 34. Although the intake and exhaust of air sterilizing system 40 are shown to be near each other, alternatively, the intake and exhaust can be distantly positioned, such as on opposite sides of volume 36. Furthermore, although no intake or exhaust ducts into and out of volume 36 are depicted in FIG. 11, alternatively actively powered or passive intake/exhaust ducts or vents can be included.

Figure 12:
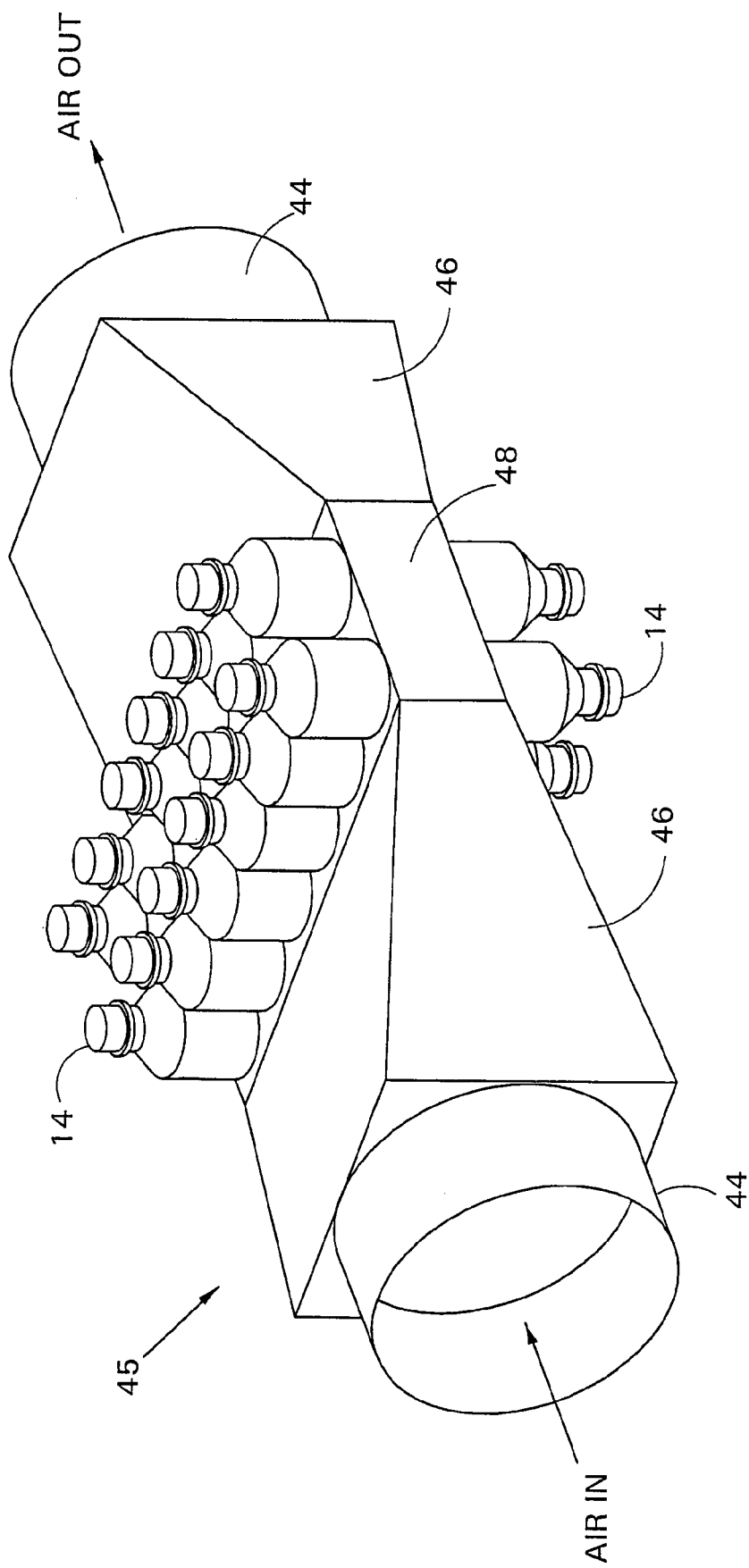
FIG. 12 is a perspective drawing of yet another embodiment of the present invention air sterilizing system.

Referring to FIG. 12, air sterilizing system 45 is yet another embodiment of the present invention that can be employed for sterilizing air flowing through a circular conduit or duct 44. System 45 includes a rectangular duct portion 48 to which opposed electron beam generators 14 are mounted. Typically, duct portion 48 has a lower height than duct 44, but is greater in width. This allows electron beam generators 14 to be employed for sufficiently treating air flowing through duct 44 with electron beams 13 which ordinarily would not have a high enough power for penetrating deeply enough through the flowing air in duct 44 to obtain sufficient treatment. Transition portions 46 connect duct portions 48 to the duct 44 on opposite sides of duct portion 48. Transition portions 46 have a height that decreases moving from duct 44 to duct portion 48 and a width that increases moving from duct 44 to duct portion 48. Typically, transition portions 46 have angled top, bottom and side walls, but alternatively, the walls can be curved. Electron beam generators 14 are abutted in side by side relation in order to provide continuous electron beam coverage across the width of duct portion 48. One or more additional rows of electron beam emitters 14 can be positioned in the direction of flow to lengthen the time of irradiation, as shown. If the height of the duct portion 48 is low enough, a single unopposed row of electron beam emitters 14 can be employed. Although a converter 16 is not depicted in FIG. 12, it is understood that such a feature can be included in system 45. In addition, the angled transition portions 46 can be employed when using two opposed electron beam generators 14 or a single electron beam generator 14.

Figure 13:
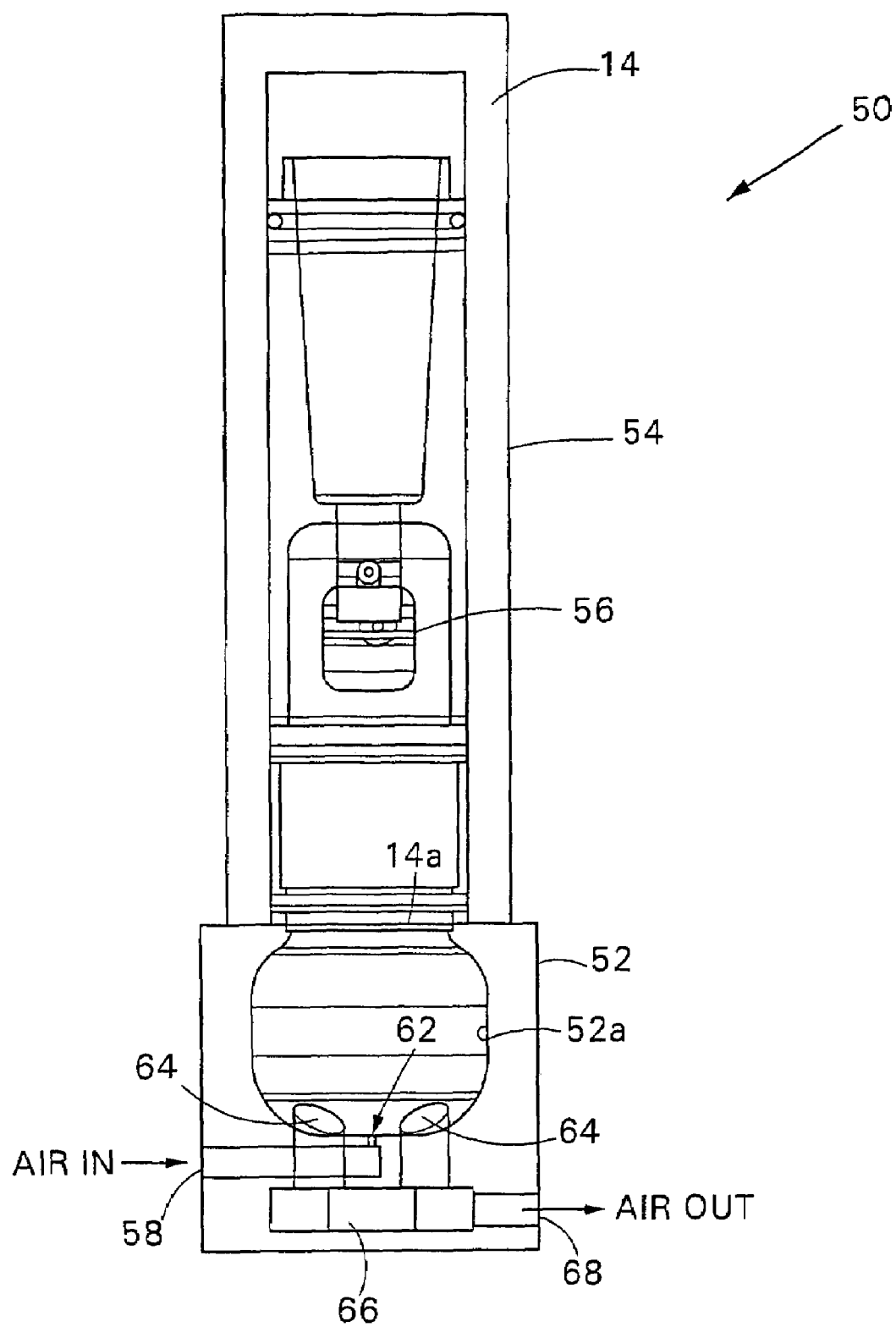
FIG. 13 is a schematic side sectional view of another embodiment of the present invention.
Figure 14:
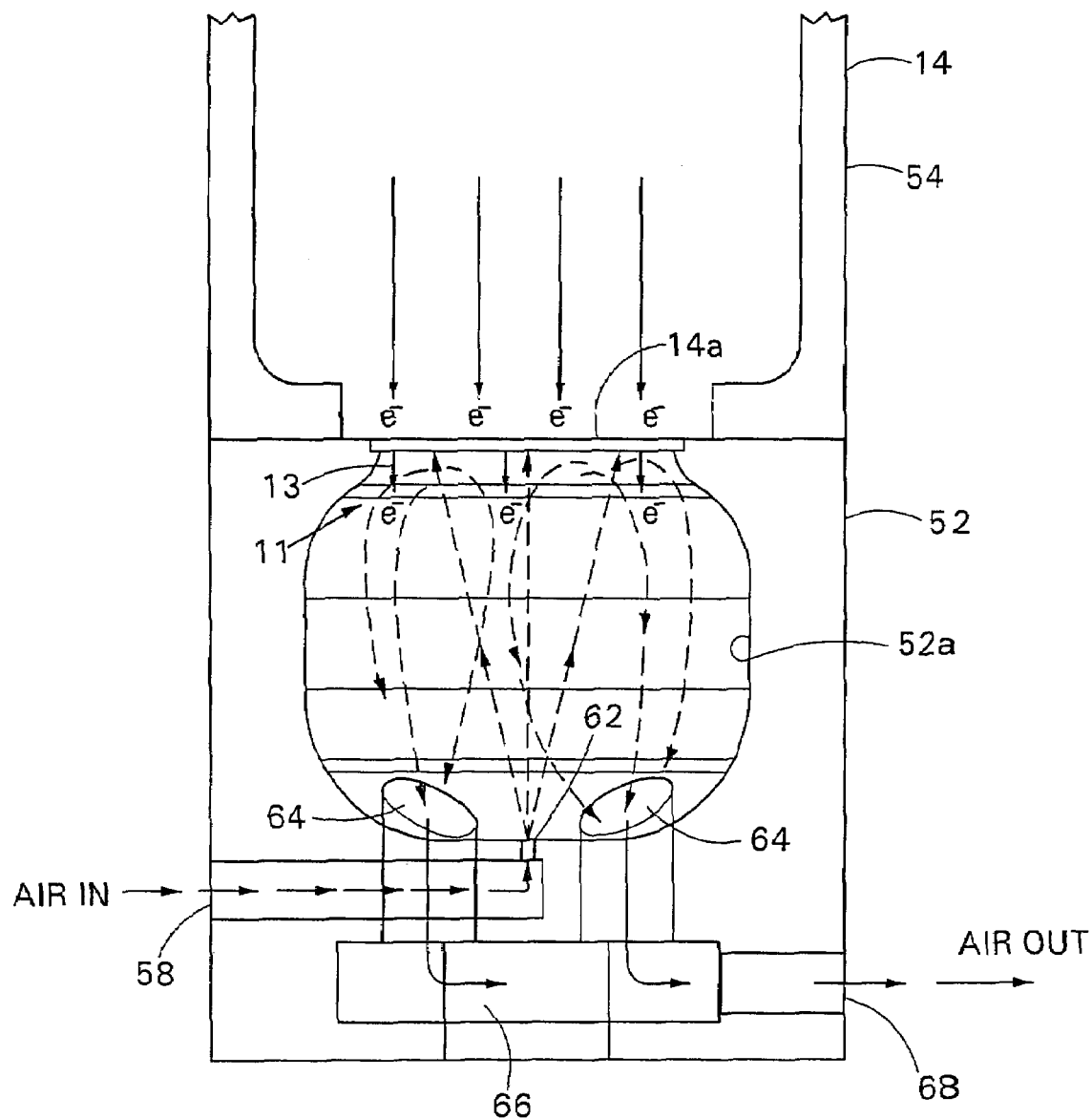
FIG. 14 is an enlargement of the bottom portion of FIG. 13.
Figure 15:
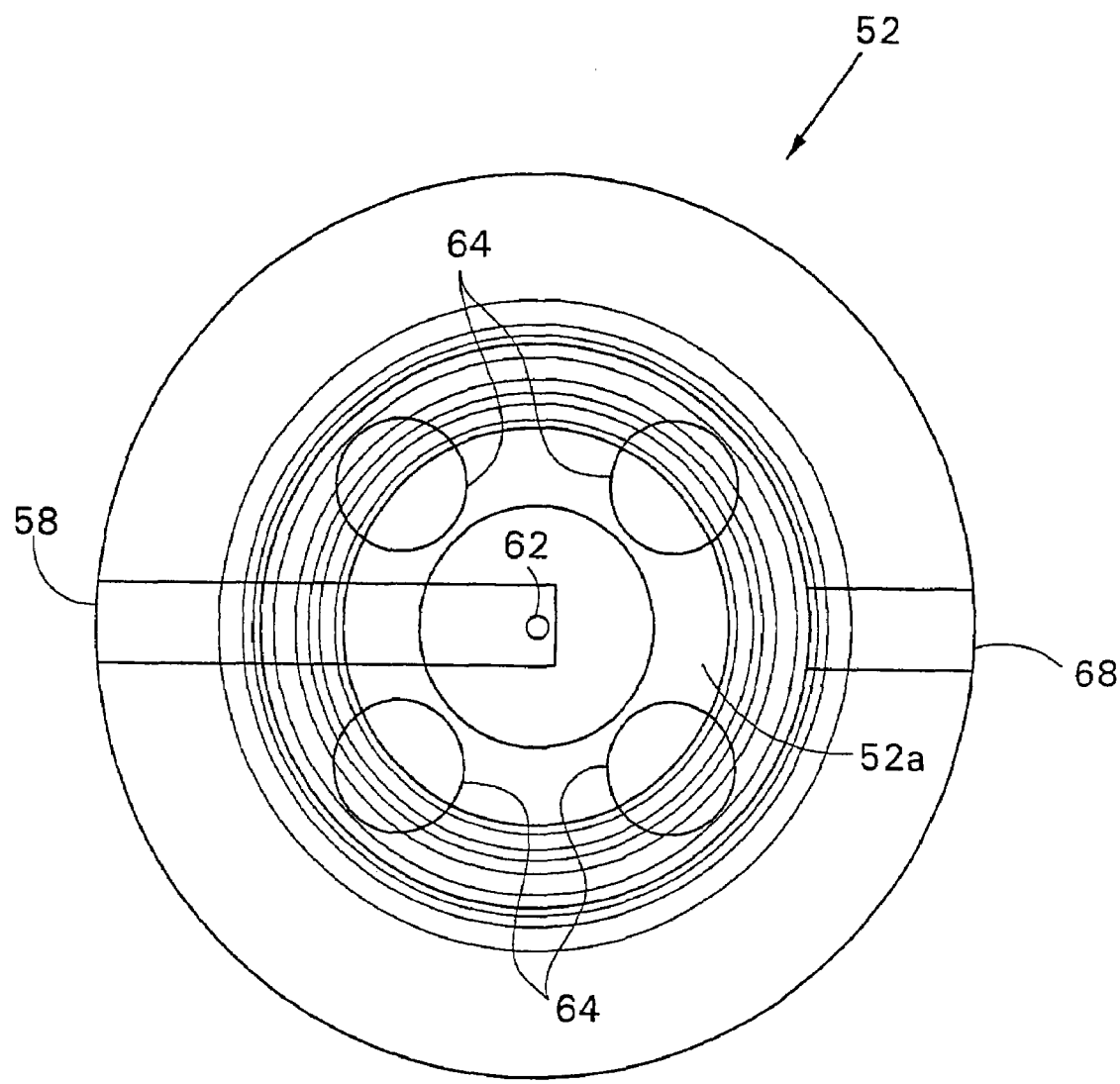
FIG. 15 is a schematic top view of the reaction chamber of FIG. 13.

Referring to FIGS. 13-15, air sterilizing system 50 is yet another embodiment of the present invention which is suitable for treating relatively small flow rates. System 50 includes a small low power electron beam generator 14 that is mounted to a reaction or sterilization chamber 52. Electron beam generator 14 includes a cylindrical housing 54 having an exit window 14a at one end. An electron gun 56 positioned within the housing generates electrons e- which are accelerated through exit window 14a in an electron beam 13. The distal end of the housing 54 of electron beam generator 14 is mounted to reaction chamber 52 in a manner where the exit window 14a is positioned and sealed over the interior cavity 52a of reaction chamber 52 so that electrons e- generated by electron gun 56 can be accelerated through exit window 14a into cavity 52a. Reaction chamber 52 has an inlet 58 through which flowing air enters. A nozzle 62 (FIGS. 14 and 15) is positioned at or near the end of inlet 58 for directing a jet of air into the cavity 52a towards exit window 14a with the central axis of the jet being substantially perpendicular to exit window 14a and generally axially or along the same direction as electron beam 13. The nozzle 62 is centrally positioned at the bottom of cavity 52a opposite to exit window 14a for uniformly directing the air towards exit window 14a. The intensity of the electron beam 13 into the flowing air increases from close to zero at the bottom of cavity 52a to about full intensity adjacent exit window 14a. Consequently, the irradiation zone 11 in the area near exit window 14a has the highest intensity of electrons e-.

The air is treated by the electron beam 13 in the irradiation zone 11 as it flows toward exit window 14a and then flows away from exit window 14a into a series of outlets 64 equally positioned about or around nozzle 62. This results in a mushroom shaped flow of substances. The air is irradiated in both the forward and backward flow directions with the increasing and decreasing electron beam irradiation intensity combining to result in relatively uniform irradiation. Consequently, cavity 52a acts as a reverse flow duct in which the flow of air reverses direction. In one embodiment, four outlets 64 are employed. The outlets 64 are in communication with a chamber 66 which is connected to the outlet 68 of reaction chamber 52 through which the treated air flows. In such an embodiment, electron beam generator 14 can have a 2 inch diameter exit window 14a and operate at about 60 kV with reaction chamber 52 having a cavity 52a of about 2 inches in diameter by about 2 inches high. In addition, any separating or filter devices 16 would be positioned downstream from the outlet 68 of reaction chamber 52. Inlet 58, nozzle 62, cavity 52a, outlets 64, chamber 66 and outlet 68, including connections to inlet 58 and outlet 68, can be considered to form a continuous duct.

Depending upon the nature of the microorganisms flowing or suspended within the circulated air, embodiments of the present invention, in some instances, can also vaporize some or all of the microorganisms. In addition to disabling or destroying the microorganisms, other biological substances flowing or suspended in the circulated air can be disabled or destroyed. These other biological substances can include biological fragments, materials, products or byproducts, for example, biological poisons, biochemical substances and byproducts, proteins, pyrogens, including endogenous pyrogens, etc. Pyrogens can include or be substances that can cause fever and/or serious illness, and can include or be bacterial endotoxins or chemicals. Biological substances that are destroyed can be vaporized, evaporated or oxidized, for example, into carbon dioxide ($CO_2$) and water ($H_2O$). As a result, the circulated air can be sterilized of biological substances, including microorganisms and other substances which can be harmful or biohazardous, or can be a contaminant in certain environments. In some situations, it can be possible that not all the disabled biological substances are vaporized or oxidized. Some of the disabled substances can have damaged structural matter or otherwise altered to be no longer harmful. In addition, biological substances can be destroyed while circulated in gases other than air.

While this invention has been particularly shown and described with references to particular embodiments thereof, it will be understood by those skilled in the art that various changes in form and details may be made therein without departing from the scope of the invention encompassed by the appended claims.

For example, instead of positioning two large electron beam generators 14 opposite to each other, alternatively, a series of small electron beam generators 14 may encircle a circular or an annular shaped air duct for radially directing a series of electron beams therein. In a rectangular duct configuration, electron beam generators 14 can be positioned on all four sides. It is understood that the air ducts described above can be rectangular, polygonal, circular or curved in cross section, and that the dimensions or cross sectional area can be varied depending upon the application at hand. Also, the size and capacity of the electron beam generators 14 can be varied to suit particular applications. Although the graphs of FIGS. 2, 3 and 5 are for electron beam generators 14 operating at about 125 kV, the shape of the curves is similar for any operating voltage or power. Additionally, various features of the air sterilizing systems described above may be combined, substituted or omitted. In all the air sterilizing systems described above, a general filter for capturing large particles and debris can be positioned upstream of the electron beam generators 14. An air circulator 32 can be positioned either upstream or downstream of the electron beam generators 14, or both. In some cases, some or all air circulators 32 may be omitted if circulation can be provided through the air ducts by other means, such as natural air currents. Furthermore, in addition to disabling biological substances in air, some contaminants in the air such as chemicals, vapors or gases, may be removed or neutralized by the present invention. Finally, the air sterilization systems of the present invention can be part of or be within an air circulation system, or can be itself an air circulation system.

What is claimed is:

1. A method of treating air comprising:

flowing the air through a duct; and irradiating the air flowing through the duct with a first electron beam from a first electron beam generator in a manner where the first electron beam sterilizes biological substances within the air.

2. The method of claim 1 further comprising treating the air within an air circulation system.

3. The method of claim 1 further comprising convening ozone within the air into oxygen with a converter positioned within the duct downstream from the first electron beam generator.

4. The method of claim 1 further comprising reflecting the electron bean with a reflector in the duct opposite to the first electron beam generator.

5. The method of claim 1 further comprising irradiating the air flowing through the duct with a second electron beam from a second electron beam generator positioned opposite to the first electron beam generator.

6. The method of claim 1 further comprising providing shielding from radiation by forming two turns in the duct an opposite sides of the first electron beam generator.

7. The method of claim 1 further comprising causing the air to flow through the duct with an air circulator.

8. The method of claim 7 further comprising positioning the duct relative to an enclosed volume for providing treated air within the volume.

9. The method of claim 1 in which at least a portion of the duct forms a reaction chamber, the method further comprising directing the air into the reaction chamber generally against the direction of the electron beam and redirecting the air generally along the direction of the electron beam for irradiating the air.

10. A system for treating air comprising:
a duct for flowing the air there through; and
a first electron beam generator positioned relative to the duct for irradiating the air flowing there through with a first electron beam in a manner where the first electron beam sterilizes biological substances within the air.

11. The system of claim 10 in which the system is in an air circulation system.

12. The system of claim 10 further comprising a convener positioned within the duct downstream from the first electron beam generator for convening ozone within the air into oxygen.

13. The system of claim 10 further comprising a reflector in the duct opposite to the first electron beam generator for reflecting the first electron beam.

14. The system of claim 10 further comprising a second electron beam generator positioned relative to the duct opposite to the first electron beam generator for irradiating the air flowing through the duct with a second electron beam.

15. The system of claim 10 in which the duct has two turns on opposite sides of the first electron beam generator for providing shielding from radiation.

16. The system of claim 10 further comprising an air circulator for causing the air to flow through the duct.

17. The system of claim 16 in which the duct is positioned relative to an enclosed volume for providing treated air within the volume.

18. The system of claim 10 in which am least a portion of the duct forms a reaction chamber, the air being directed into the reaction chamber generally against the direction of the electron beam and then redirected generally along the direction of the electron beam for irradiating the air.

* * * * *

UNITED STATES PATENT AND TRADEMARK OFFICE
CERTIFICATE OF CORRECTION

PATENT NO. : 7,547,892 B2  Page 1 of 1
APPLICATION NO. : 11/703620
DATED : June 16, 2009
INVENTOR(S) : Tzvi Avnery It is certified that error appears in the above-identified patent and that said Letters Patent is hereby corrected as shown below:

Column 8

Claim 3, Line 64, delete "convening" and insert --converting--

Column 9

Claim 6, Line 9, delete "an" and insert --on--

Column 10

Claim 12, Line 3, delete "convener" and insert --converter--

Claim 12, Line 5, delete "convening" and insert --converting--

Claim 18, Line 22, delete "am" and insert --at--

Signed and Sealed this

Eighteenth Day of August, 2009

David J. Kappos
*Director of the United States Patent and Trademark Office*